(12) United States Patent
Tesanovic et al.

(10) Patent No.: US 9,129,459 B2
(45) Date of Patent: Sep. 8, 2015

(54) DETECTING OPERATING MODE OF HYBRID VEHICLES

(71) Applicant: FUJITSU LIMITED, Kawasaki-shi, Kanagawa (JP)

(72) Inventors: Milos Tesanovic, Harrow (GB); Sunil Keshavji Vadgama, Ashford (GB)

(73) Assignee: FUJITSU LIMITED, Kawasaki (JP)

(*) Notice: Subject to any disclaimer, the term of this patent is extended or adjusted under 35 U.S.C. 154(b) by 0 days.

(21) Appl. No.: 14/255,041

(22) Filed: Apr. 17, 2014

(65) Prior Publication Data
US 2015/0006018 A1 Jan. 1, 2015

(30) Foreign Application Priority Data
Jun. 28, 2013 (EP) .................................... 13174369

(51) Int. Cl.
*G07C 5/08* (2006.01)
*G01N 21/3504* (2014.01)
*G08G 1/015* (2006.01)
*G08G 1/04* (2006.01)
*G08G 1/00* (2006.01)
*G07C 5/00* (2006.01)
*G01N 21/17* (2006.01)

(52) U.S. Cl.
CPC .......... *G07C 5/0808* (2013.01); *G01N 21/3504* (2013.01); *G07C 5/008* (2013.01); *G08G 1/015* (2013.01); *G08G 1/04* (2013.01); *G08G 1/207* (2013.01); *G01N 2021/1793* (2013.01); *G01N 2021/3531* (2013.01)

(58) Field of Classification Search
CPC ........ G07C 5/008; G07C 5/0808; G08G 1/04; G08G 1/015; G08G 1/207; G01N 21/3504; G01N 2021/1793; G01N 2021/3531

USPC .......................................................... 701/29.6
See application file for complete search history.

(56) References Cited

U.S. PATENT DOCUMENTS

| | | | |
|---|---|---|---|
| 5,489,777 A * | 2/1996 | Stedman et al. ........... 250/338.5 |
| 5,583,765 A * | 12/1996 | Kleehammer .................... 701/1 |
| 5,719,396 A | 2/1998 | Jack et al. |
| 6,307,201 B1 * | 10/2001 | Didomenico et al. ... 250/339.13 |
| 7,141,793 B2 * | 11/2006 | Johnson et al. ............. 250/338.5 |
| 8,937,559 B2 * | 1/2015 | Ioli ............................ 340/932.2 |
| 2002/0092988 A1 * | 7/2002 | Didomenico et al. ...... 250/338.5 |
| 2004/0081221 A1 * | 4/2004 | Sandvoss ...................... 374/130 |

(Continued)

OTHER PUBLICATIONS

Extended European Search Report mailed Dec. 5, 2013 in corresponding European Patent Application No. 13174369.2-1803.

*Primary Examiner* — Mary Cheung
*Assistant Examiner* — Atul Trivedi
(74) *Attorney, Agent, or Firm* — Staas & Halsey LLP

(57) ABSTRACT

A method for detecting the operating mode of a hybrid vehicle using roadside cameras, said method including the analysis of thermal images of parts of the vehicle and/or exhaust fumes, in combination with associated images of the number plates obtained using visual camera(s) operating in synchronism with said thermal camera and used for vehicle make inference and driver identification. The inferred make of the car is used for aforementioned analysis of thermal images. In a variant, the method is used to verify an operating mode reported by, or obtained from information reported by, the vehicle itself. The method can be used in a pollution management system for calculating financial charges to vehicle drivers in a low-emission zone of a Smart City for example.

13 Claims, 3 Drawing Sheets

(56) References Cited

U.S. PATENT DOCUMENTS

| | | |
|---|---|---|
| 2004/0104345 A1 | 6/2004 | Kansakoski et al. |
| 2006/0047445 A1* | 3/2006 | Williams et al. ................. 702/30 |
| 2007/0263213 A1* | 11/2007 | Stedman ........................ 356/328 |
| 2009/0018721 A1* | 1/2009 | Mian et al. ...................... 701/33 |
| 2009/0171549 A1* | 7/2009 | Hyde et al. .................... 701/102 |
| 2010/0076878 A1 | 3/2010 | Burr et al. |
| 2010/0280705 A1* | 11/2010 | Eckhoff et al. ................. 701/33 |
| 2010/0280706 A1* | 11/2010 | Eckhoff et al. ................. 701/33 |
| 2010/0280707 A1* | 11/2010 | Eckhoff et al. ................. 701/33 |
| 2010/0280708 A1* | 11/2010 | Eckhoff et al. ................. 701/33 |
| 2011/0106354 A1* | 5/2011 | Eckhoff et al. ................. 701/22 |
| 2011/0106591 A1* | 5/2011 | Eckhoff et al. .............. 705/14.1 |
| 2011/0153223 A1* | 6/2011 | Gentala et al. ................. 702/24 |

* cited by examiner

S10
Detect Presence of Vehicle
|
S12
Take Visual Image
|
S14
Identify Vehicle
|
S16
Take Thermal Image
|
S18
Determine Operating mode
|
S20
Calculate Pollution Charge

DETECTING OPERATING MODE OF HYBRID VEHICLES

CROSS-REFERENCE TO RELATED APPLICATIONS

This application claims the benefit of application Ser. No. 13/174,369.2, filed Jun. 28, 2013, the disclosure of which is incorporated herein by reference.

BACKGROUND

1. Field

The present invention relates to detecting the current operation mode of vehicles for the purposes of vehicle emission control, including the operating mode of hybrid vehicles such as, but not restricted to, hybrid electric vehicles (HEVs).

2. Description of the Related Art

Conventional motor vehicles such as cars and trucks employ an internal combustion engine (ICE) running on petrol or diesel fuel. By contrast, hybrid vehicles use a mixture of power or fuel sources. A subclass of hybrid vehicles is the hybrid electric vehicle, or HEV. Hybrid vehicles use an electric motor, powered by a battery and/or by a generator, in addition to the ICE. So-called "full" hybrids can operate on fuel by running the internal combustion engine, on stored electrical power by running the electric motor, or a combination of both. However, the term "hybrids" in this specification also covers vehicles capable of running an internal combustion engine on alternative fuels, such as liquefied gas in place of petrol or diesel fuel, to reduce vehicle emissions. These various ways of operating a hybrid vehicle are referred to as "operating modes" henceforth.

Hybrid vehicles are viewed as a key contributor to reduction of pollution in urban areas. Nowadays, the majority of air pollution in urban areas comes directly from road traffic rather than industry. Road traffic is considered to be responsible for 25% of all emissions in Europe. Moreover, CO2, which is a major product of ICE car emissions, is a greenhouse gas. Efforts are being made to reduce air pollution and its consequent environmental impacts, especially in urban areas. These efforts include, for example, providing incentives for urban drivers to purchase and drive a hybrid vehicle rather than a conventional ICE-based car. London's congestion charge, which exempts HEVs as well as cars which emit 100 g/km or less of CO2 and which meet the Euro 5 standard for air quality, is one example. However, such incentives to date do not take account of in what operating mode vehicles are actually driven.

Thus, for drivers to run their hybrid vehicles in an operating mode which reduces pollution is of great importance to reducing the emissions of CO2 and other pollutants. The operating mode currently in use is normally set by the driver, although this may include a setting in which the vehicle selects the most appropriate operating mode automatically.

The concept of the "Smart City" is meanwhile receiving attention. This term refers to a city in which various departments and services are interconnected, and in which a large-scale network of sensors is deployed, the sensor readings being used to monitor various parameters such as traffic congestion and pollution. This enables transport and other services to be kept running smoothly and to some extent autonomously: for example traffic congestion information may be used to manage traffic lights.

One aspect of the Smart City is pollution management by, for example, restricting use of vehicles at certain times of day and/or in certain geographical zones (low-emission zones) so as to restrict the buildup of pollutants in the air. This is referred to henceforth as a pollution management system. A conceivable pollution management system might, for example, involve vehicle recognition linked to a database of pollution levels for different types (makes and models) of vehicle. In this way, a driver of a highly-polluting vehicle might find themselves barred from entering a low-emission zone at least during certain periods. Alternatively, it is possible to envisage systems which do not simply either bar or allow certain types of vehicles, but allow many (or even most) vehicles to be driven, provided they operate in a certain mode and/or the driver/owner pays an appropriate fee (below referred to as an "emission charge"). This will give the citizens a greater freedom and flexibility without compromising the environment. Embodiments to be described later will focus on a pollution management system of this type, where vehicle usage is influenced by pricing rather than by barring certain vehicles outright.

With the proliferation of hybrid vehicles (vehicles that use a mixture of power or fuel sources), the distribution of pollution contributions from various makes of cars becomes increasingly variable. If pollution management is to adapt to this trend, it will no longer be sufficient to simply match a vehicle to a single pollution category based on the automated recognition of its number plates at the designated check point (usually a point of entry into a pollution-critical area).

Design of a potential solution is complicated by the fact that various hybrids will contribute a widely varying degree of pollutants depending on the mode they are operating in (dropping down to no pollutants at all when they are operating in an electric-only mode, as in the case of HEVs). It is important to be able to control, or levy financial charges for, vehicle usage based on which operating mode vehicles are actually being driven in, rather than based on the theoretical benefits of an operating mode which might be used only rarely.

Techniques have been proposed for remotely determining vehicle emissions from moving vehicles. Until now, however, there has been no consideration of the various operating modes available to hybrid vehicles, or for providing a pollution management solution which takes such operating modes into account.

SUMMARY

Additional aspects and/or advantages will be set forth in part in the description which follows and, in part, will be apparent from the description, or may be learned by practice of the invention.

According to a first aspect of the present invention, there is provided a method of managing vehicle emissions including:
  receiving at least one measurement relating to a vehicle and including a thermal measurement indicative of emissions from the vehicle;
  detecting an identity of the vehicle and from the detected identity, determining one or more operating modes available to the vehicle; and
  inferring, from the thermal measurement, a said operating mode in use by the vehicle.

Although the above method (referred to below as "the basic method") is aimed primarily at hybrid vehicles, it is not restricted to use only with hybrid vehicles. Conventional ICE-only vehicles or electric-only vehicles are considered as vehicles having only one operating mode.

Preferably, the method further includes calculating an emission charge for the vehicle, based on the operating mode inferred. The emission charge refers to a financial levy, preferably varied in dependence on the operating mode, for usage of the vehicle at a location (such as a low-emission zone) where the at least one measurement is taken and/or for a certain time period. Calculating an emission charge includes the possibility of a zero charge, for example for a vehicle running in a zero-emission mode. Performing the method for many vehicles passing by or stopping at a given location, enables management of traffic pollution in the vicinity of the location.

The method preferably further includes providing at least one visual imaging device for use in detecting the identity of the vehicle. This may be provided in the vicinity of a road along which vehicles travel, and may be located at an entrance to a low-emission zone for example. One or more image of the vehicle (or of part of the vehicle, such as its registration plate) may be captured, and then processed to yield the vehicle make/model, and/or registration number, which can then be matched with entries in a vehicle database so as to identify the vehicle. Alternatively, or in addition, the vehicle identity can be detected by means of an in-car transponder or the like. By identifying the vehicle, in particular its make/model, it is possible to know the operating modes available to that vehicle.

Preferably, there is also provided at least one thermal imaging device for detecting a thermal image indicative of the vehicle emissions, the thermal image used to derive the thermal measurement. The thermal imaging device need not be in the same physical location as any visual imaging device referred to earlier.

Such a thermal imaging device, for example an infrared (IR) camera, may detect a thermal image of one or more portions of the vehicle. This can yield a "thermal signature" to assist in inferring the operating mode, since different operating modes can be expected to produce different thermal signatures. The thermal signature may characterize the operating mode by the relative brightness within the thermal image of each vehicle portion. Portions of the vehicle to be imaged in this way may include the exhaust system, engine, and/or parts of the vehicle chassis. Thus, for example, in a thermal image in which brighter areas indicate higher temperatures, the exhaust system may be relatively dark for a vehicle in a low-emission or zero-emission mode, compared with when the same vehicle is using the ICE normally.

In an embodiment of the present invention, since the locations of the appropriate portions to be considered in such thermal imaging will depend on the vehicle type and configuration, the one or more portions are selected in dependence on the identity of the vehicle.

In an embodiment of the present invention, to assist the thermal imager in locating the portions to be thermally imaged, they are located by their relative positions to the number plate.

Although the method of the invention will typically involve the use of one or more thermal imaging devices installed at a roadside for detecting passing traffic, this is not the only way of receiving the thermal measurement. In an embodiment, the vehicle provides the thermal measurement employed in the basic form of the method.

More generally, the vehicle may provide data indicative of emissions from the vehicle and including one or more of:
 a thermal measurement of an exhaust part;
 a thermal measurement of at least one other part of the vehicle;
 a chemical measurement of exhaust emissions; and
 the operating mode in use by the vehicle.

Here, "chemical" measurement means a measurement of one or more chemical constituents of the exhaust gases, in other words some indication of composition of the exhaust emissions.

In a preferred form, this data is generated at least partly by a smart exhaust system of the vehicle as defined below. The operating mode would generally be provided by a central controller or on-board computer of the vehicle.

It is preferable, particularly for verification purposes, to be able to link data received from a vehicle with a date/time and a location. Therefore, the method preferably further includes applying a time stamp and location stamp to the data provided from the vehicle.

In a variant of the method, the vehicle provides data in the form of at least one thermal measurement, chemical measurement, a direct indication of operating mode and/or additional data and the above basic method is employed for verifying the data from the vehicle. That is, by receiving data from the vehicle in the above manner, it becomes possible to verify an operating mode indicated (either directly or indirectly via thermal/chemical measurements) by the vehicle, with the operating mode inferred from a thermal measurement taken outside of the vehicle (for example by a roadside thermal imager).

Therefore, in the variant of the method, the receiving step includes receiving a thermal measurement taken outside the vehicle and the method further includes selectively verifying the data provided from the vehicle with the result of inferring based on the thermal measurement taken outside the vehicle.

The method (basic method and/or the above variant) may further involve the thermal imaging device detecting a thermal image of the vehicle emissions. This can be used to estimate the volume, and potentially also the composition, of the vehicle emissions. Absence of vehicle emissions may be detected and used to infer that the vehicle is operating in a zero-emission mode.

Thus, an embodiment of the present invention is a method of managing vehicle emissions including:
 receiving at least one measurement relating to a vehicle, including a thermal measurement indicative of emissions from the vehicle; and
 detecting an identity of the vehicle; characterized by:
 from the detected identity, determining one or more operating modes available to the vehicle, different operating modes having different thermal signatures;
 by at least one thermal imaging device, detecting a thermal image of one or more portions of the vehicle indicative of the operating mode;
 deriving a thermal signature from the thermal image; and
 inferring, from the thermal signature, a said operating mode in use by the vehicle.

In one embodiment, the at least one measurement further includes a measurement indicative of composition of the vehicle emissions. This can allow a check of the presence and/or amounts of specific pollutants and for the emission charge to be adjusted accordingly. This measurement can either be made by a sensor external to the vehicle, or reported from the vehicle's smart exhaust system as referred to above.

According to a second aspect of the present invention, there is provided a pollution management system including:
 a central control unit;
 at least one camera coupled to the central control unit, for taking at least one visual image of a vehicle;
 at least one thermal detector for making a thermal measurement indicative of emissions from the vehicle; and at least one database accessible to the central control unit for providing information on vehicle types and operating modes; wherein
the central control unit is arranged to receive the thermal measurement from the thermal detector; detect an identity of the vehicle using the visual image from the camera and from the detected identity, determine one or more operating modes available to the vehicle; and infer, from the thermal measurement, a said operating mode in use by the vehicle.

The central control unit may further calculate an emission charge for the vehicle, based on the operating mode inferred, on the principle that certain operating modes are more polluting than others.

The central control unit can be operated in accordance with any of the methods outlined above. The thermal detector may be a thermal imaging device as previously mentioned (and although generally a roadside thermal imager, could also be located on the vehicle). Many different locations around or within a given geographical area may be equipped with respective visual cameras and thermal detectors. By processing data of all the vehicles (not necessarily only hybrid vehicles) within a given geographical area, the central control unit can provide a pollution management system for that area. The central control unit may control many individual geographical areas constituting a whole city, region or even an entire country.

Where vehicles are equipped with the smart exhaust system referred to earlier, it becomes possible to check data received from vehicles with evidence provided by roadside thermal imagers. Thus, in one embodiment the central control unit is operable selectively to verify reports from the vehicle. This can be achieved in that the central control unit is further arranged to: receive data from a vehicle indicative of the vehicle emissions; extract or infer from that data the operating mode of the vehicle; decide (randomly, based on periodic sampling, or in some other way) to verify the operating mode; and infer the operating mode in use by the vehicle on the basis of a thermal measurement as already defined above.

According to a further aspect of the invention, there is provided a smart exhaust system suitable for use in the above method or pollution control system, capable of analyzing exhaust emissions for the purpose of automated fault diagnostics, and for the purpose of communicating the emission amounts to emission data collection & emission policing systems. The smart exhaust system may include at least one sensor disposed within the exhaust pipe for detecting presence of at least one specific constituent (gas or particulates) within the exhaust emissions, and a transmitter arranged to transmit sensor readings to a remote data collector such as at a roadside.

The smart exhaust system may further include a clock and a location device for enabling a time stamp and a location stamp to be applied to data relating to the exhaust emissions. The smart exhaust system need not be wholly located within an exhaust part of the vehicle, but may be distributed. The smart exhaust system may further be coupled to a vehicle control system allowing, for example, the operating mode as set by the control system to be included in the data provided by the vehicle.

To summarize, embodiments of the present invention may provide a method for inferring the mode (specific combination of power or fuel sources) a hybrid vehicle is running in, using roadside cameras (visual and thermal). A thermal camera is used to detect the temperature signatures of the exhaust pipe/engine/parts of chassis, and image processing is then applied which looks for matches inside a database including various modes for various makes of cars. Coupled with this thermal camera is at least one visual camera which captures the vehicle registration number used to infer the make of the car. In variants, this basic method is augmented by a report from the vehicle itself, for example from a smart exhaust system, to indicate (directly or indirectly) the vehicle's operating mode, the basic method employing roadside data then allowing verification of the reported operating mode.

The coupling of the thermal and the visual light camera(s) is beneficial for at least two reasons:
It enables savings in thermal image processing by reducing the number of sampling points of the thermal image in ways disclosed in this invention; and
It provides proof of potential infringement admissible in many courts of law.

Particular embodiments further use the thermal camera to detect the presence of fumes, and estimate the volume of exhaust fumes using 3D thermal imaging.

In this way, the present invention enables a pollution management system to be implemented which monitors the operating modes of vehicles such as hybrid vehicles and as such enables efficient policing of low-emission zones in future Smart Cities. Embodiments enable the detection of a widely varying collection of modes and not merely whether a vehicle is being run in a zero-emission mode or not. Additionally, by coupling the operations of thermal and visual cameras, savings in processing are enabled by allowing precise location of the exhaust with respect to the number plates/ground to be inferred, thereby enabling analysis of the thermal image using fewer samples.

BRIEF DESCRIPTION OF THE DRAWINGS

These and/or other aspects and advantages will become apparent and more readily appreciated from the following description of the embodiments, taken in conjunction with the accompanying drawings of which.

DETAILED DESCRIPTION

Figure 1:
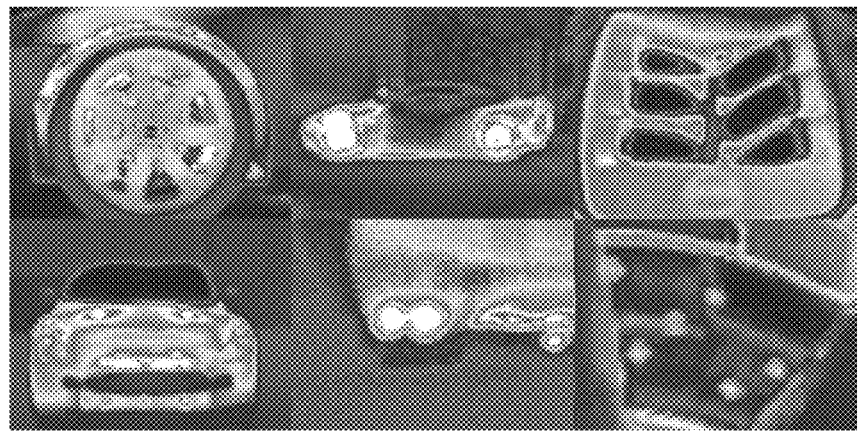
FIG. 1 is a set of thermal images of a car running on an internal combustion engine.

Reference will now be made in detail to the embodiments, examples of which are illustrated in the accompanying drawings, wherein like reference numerals refer to the like elements throughout. The embodiments are described below to explain the present invention by referring to the figures.

A hot body (an object at a temperature higher than that of its surroundings) radiates infrared radiation. Thermal imaging allows this radiation to be visualized, and reveals the distribution of temperature over the hot body since the wavelength of infrared radiation varies with temperature.

A principle of the invention is to use thermal imaging for mode recognition of vehicles, by detecting the temperature signature of the exhaust pipe/engine/parts of chassis and to match that signature to a bank of thermal signatures (for exhausts/engines/chassis etc.) for various makes of cars operating in different modes.

FIG. 1 is a set of thermal images of a car running on an internal combustion engine, in this case a Nissan GT-R sports car. The images in FIG. 1 are of different views or portions of the car, namely (clockwise from top left) wheel, side body, engine compartment, brake disc (as exposed through one wheel), rear body including twin exhaust pipes, and front. The different shadings (corresponding to colors in the original image) denote differing brightness levels within the thermal image and thus, differing temperature levels. The above-mentioned "temperature signature" includes the relative brightness of the individual images. Although FIG. 1 shows the car operated in ICE mode, a hybrid version of the GT-R (which was at least proposed if not marketed), would produce a different set of images if operated in a low-emission mode, particularly with respect to the exhaust.

Here, the term "temperature signature" may simply refer to a thermal image, but can also encompass more advanced processing of that image such as its spectral characteristics (wavelength distribution). This allows an inference to be made about the level of pollution presently being caused by the vehicle.

Figure 2:
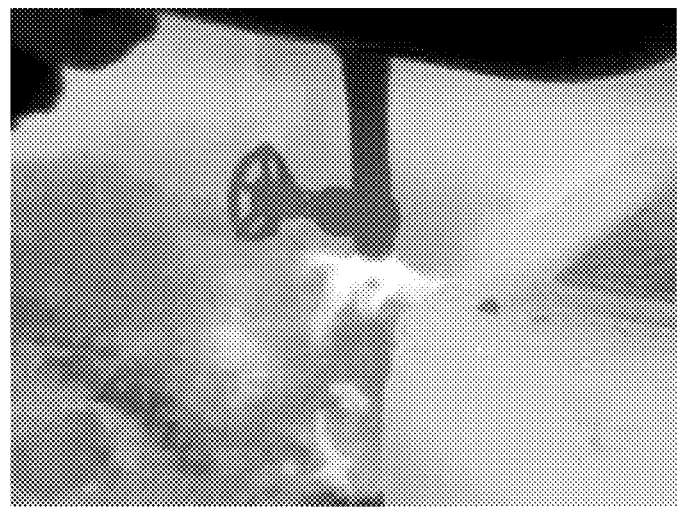
FIG. 2 is a thermal image of a gaseous emission from a pipe.

The pollution level can also be assessed more directly by, for example, imaging the exhaust emissions of the vehicle. Use of thermal imaging for gas leaks detection is well-known; see FIG. 2 for an IR image of a gas leak. FIG. 2 shows a valve leaking ethylene, which shows up as white smoke in the black-and-white hot thermal image (from http://www.flir.com/cs/emea/en/). In the same way, it is possible to thermally image exhaust gases leaving the exhaust system of a vehicle.

The above principle may be applied to moving vehicles as they pass a roadside thermal imager. It may also be applied to a place where vehicles come to rest for a short time, such as a road junction with a stop sign or traffic lights. Such a road junction may be the entrance to a low-emission zone of a Smart City for example. Another possible implementation would be at a toll gate at which vehicles exit a motorway in order to enter a city zone. One or more such installations, coupled to a central control entity (central control unit), provide a pollution control system as will now be described.

Figures 3, 4:
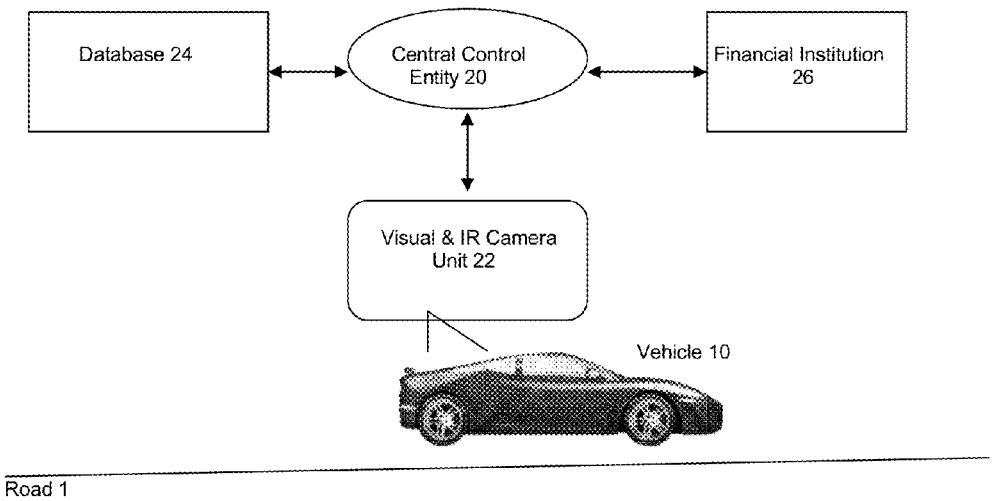
FIG. 3 shows the overall system architecture in one embodiment of the invention.
FIG. 4 is a flowchart of process steps in a basic method of the present invention.

FIG. 3 shows the system architecture in one embodiment. It is assumed that vehicles 10 are moving along a stretch of road 1 beside, above or otherwise adjacent to which is located a camera unit 22, for example at a junction as already mentioned.

For simplicity, it is further assumed that vehicles 10 are travelling in single file, one by one and either halt briefly opposite the camera unit, or pass slowly by. The vehicle is potentially any vehicle but in particular may be a hybrid vehicle having more than one operating mode. As is the case in most countries, the vehicle has number plates mounted front and back, bearing a registration number (license number) in the form of letters and numbers which can be used to uniquely identify the vehicle.

In this embodiment, the camera unit 22 includes both a visual camera (visible light camera) and an IR (infrared) camera. It may be possible for both cameras to be provided by a common imaging device or at least integrated into the same unit. The camera unit 22 is connected to a central control unit 20 for at least receiving images from the camera unit 22. The central control unit 20 may be part of a pollution management system for a Smart City, and may have other functions apart from pollution control such as traffic congestion management, traffic light management and so forth. This central control unit 20 in turn is connected to a database 24 of vehicle makes/models, and/or vehicle registration numbers; and optionally to a financial institution such as a bank for use in billing a vehicle owner's bank account with a emission charge (in other words a vehicle usage charge dependent on the operating mode used).

FIG. 4 is a flowchart of the operation in embodiments.

Firstly, operation is triggered by detecting in some way the presence of a vehicle (S10). This can be done in any conventionally-known manner such as placing a pressure detector on or under the road surface, or a motion detector by the road side. Next, a visual image of the vehicle is taken (S12). For example at least the front of the vehicle is photographed as it approaches the camera unit so as to capture the front number plate of the vehicle.

Next, in step S14 the central control unit 20 processes the image data from the camera unit 22 so as to identify the vehicle on the basis of the visual image (for example an image of the number plate, which can be subjected to optical character recognition) by matching it with an entry in the database. Identifying the vehicle by number plate allows not only the owner to be established, but also the make (manufacturer) and model of vehicle. This information can be used as a guide for thermally imaging appropriate portions of the vehicle as explained below.

Then, at least one infrared image is captured (step S16). Given sufficient time and/or variety of imaging thermal imagers, a set of images similar to that shown in FIG. 1 may be obtained, but tailored to determination of operating mode (for example it may be unnecessary to image the wheels or brakes). In step S18 the central control unit 20, having identified the vehicle, works out which operating mode the vehicle 10 is running on, based on the thermal image(s) and information about the thermal signatures of various operating modes of that vehicle type, which information is either stored in the same database or obtained by interrogating a separate database.

Finally (S20), the central control unit 20 calculates a financial charge appropriate to the operating mode of the vehicle 10, and generates a bill or directly debits the account of the vehicle owner, via the financial institution 26. The amount billed (vehicle usage charge) may vary in accordance with various factors in addition to operating mode, such as location, time of day, or season/weather. Vehicles not present in the database for any reason, such as foreign-registered vehicles, may be charged at the highest rate. Instead, or in addition, to levying a financial penalty on more polluting vehicles/operating modes, certain vehicles may be barred from proceeding further (into a pollution-controlled city centre for example) if they are grossly polluting.

The efficiency and accuracy of this procedure is significantly increased if the sampling of the thermal image is synchronized with the visible light camera detecting the number plate. The location of the number plate with respect to exhaust assembly (or other parts of the vehicle whose temperature signatures are being captured) can be obtained from the information on the make and model of the car. This in turn determines the sampling points of the thermal image. There is no need to be restricted to a single sampling point: several samples (thermal images) may be taken.

For example, if one portion to be thermally imaged is the exhaust system (as would typically be the case), in many types of vehicle this is to be found to the left of and downwards from the rear number plate when the vehicle is viewed from the back. This increases the efficiency and accuracy of a thermal imaging camera which would otherwise be in continuous search & detect operation, in addition to also enabling thermal cameras to only take a limited number of images, or only power up occasionally, thereby conserving power. Taking a reduced number of images minimizes the local memory requirements as well as transmission link capacity to the central control unit 20.

As explained, it helps the accuracy if the two cameras are synchronized but this does not necessarily mean that they will be taking pictures at precisely the same instant. This is due to the processing and transmission delay incurred by the fact that once the "regular" camera takes a snapshot of the number plates, the system needs to look up the make and model, identify the exact location of the parts of interest with respect to the number plate. The system then uses this information to specify the exact location in time and space for infra-red (IR) image capturing. The delay in time can be estimated based on the speed of the vehicle.

In the case of applying the invention to roadside detection of moving vehicles, the vehicle may be moving too quickly for the necessary processing to be completed in time to activate the IR camera. Also, there are no guarantees that a vehicle will not slow down or stop, thus being overtaken by a different vehicle before the check-point is reached. Therefore, in an alternative embodiment, a second visual camera is provided before (upstream of) the thermal camera with respect to the line of approach of vehicles.

Figure 5:
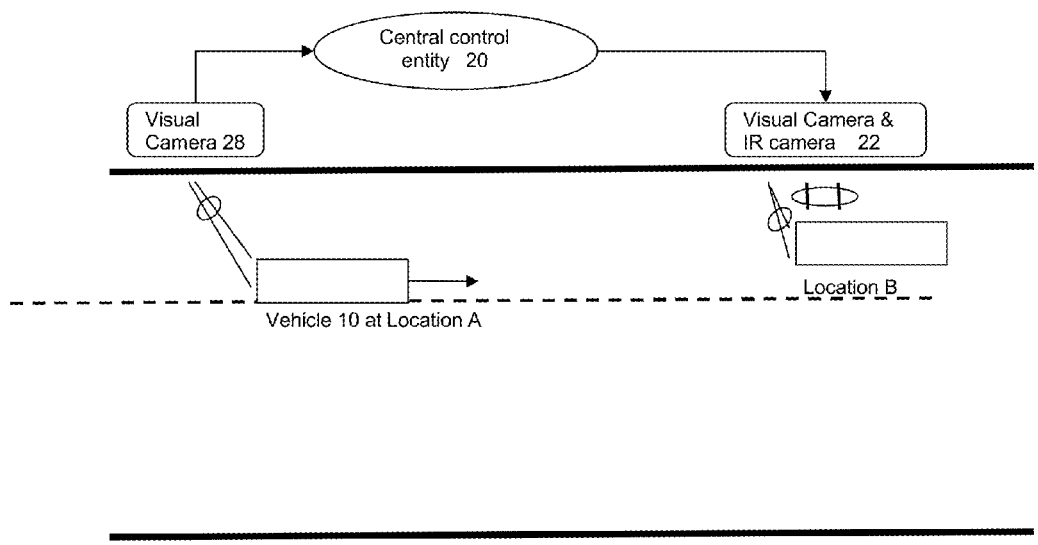
FIG. 5 shows a system architecture in an alternative embodiment.

FIG. 5 shows the system architecture in this embodiment. Although not shown, the database 24 and financial institution 26 (if required) are present also in this embodiment.

In this architecture, an upstream visual camera 28 (see FIG. 5) initially captures the number plate of a vehicle 10 (at location A) approaching a check-point (lying at location B ahead) and feeds the registration back to the central control entity 20. The central control entity 20 retrieves the vehicle details from the database 24 on the basis of the registration number and, based on the make of the vehicle, sends the instructions for thermal image capture together with the vehicle registration number. The thermal camera in unit 22 performs the required capture, simultaneously with the (downstream) visual camera of unit 22 which is used to ensure the prescribed thermal image capture protocol is being applied to the correct vehicle (as well as to offer proof of deviation from required mode admissible in a court of law). The visual camera in unit 22 is not required if the vehicle identification could be performed equally reliably by the more remote (relative to location B) upstream visual camera 28.

As a refinement, it is envisaged that an additional (and potentially much cheaper) IR camera could be integrated with or at least co-located with the upstream visual camera 28. This IR camera would perform a "crude" (hot/cold) temperature detection of parts of the vehicle. If e.g. the exhaust is cold then there is little point in taking any IR images using the IR camera further down the road (within the downstream unit 22) i.e. this "main" thermal camera at location B can power down. Since some image-capturing photo-arrays are sensitive to near-IR light, it would be possible for the same imaging device to provide both the upstream IR camera and the upstream visual camera 28.

In another embodiment, thermal imaging is employed not only for determining the operating mode of the vehicle, but also for exhaust fumes detection, the principle of which was already mentioned with respect to FIG. 2.

Detection of exhaust emissions can be used on its own (if say the exhaust is inaccessible), or used in combination with vehicle thermal imaging for higher accuracy. Fumes presence and temperature detection is more susceptible to background (thermal) noise than the exhaust temperature detection. Therefore, one measure to facilitate identification of the operating mode is to require vehicles to halt one at a time at a checkpoint for detection of the exhaust emissions. Another measure, during the process of creating the bank of images (database 24) is to include thermal signatures not only of vehicle portions under various operating modes, but also the impact of operating mode upon the exhaust emissions. As a simple example, a zero-emission mode would involve no exhaust emission, or a low-emission mode creating only water vapor would create a different thermal image than normal ICE operation.

More generally, different mixtures of input fuels (the term "modes" includes this possibility) will have different infra-red (IR) spectral characteristics of respective exhaust fumes. In other words, even in this meaning of the word "mode", different modes will have different temperature signatures and spectral characteristics of the exhaust fumes (with possible nuances in the exhaust signature/temperature levels), and this is especially useful when more than one mode of the same vehicle utilizes an ICE.

An additional embodiment of the present invention attempts to measure the pollution level of a given vehicle directly rather than (or as well as) inferring it from an operating mode of the vehicle.

Having successfully detected the mode and hence knowing which mixture of input fuels is being used, it is possible to estimate the amount of pollution generated, by using 3D (stereo) IR cameras to estimate the volume of the gas, and combining this with the previously inferred composition of the gas.

Alternatively, the chemical composition of the gas can be determined in a more traditional way by using "sniffers". (However traditional "sniffers" would be generally impractical for vehicles moving at regular road speeds.) Thus it becomes feasible to estimate for example the $CO_2$ contribution of the vehicle and mode in question.

3D imaging can additionally (or alternatively) be used to obtain more accurate heat signatures and spectral signatures.

Further embodiments of the invention combine the pollution control system already described with reports from the vehicle itself. In other words the vehicle provides the thermal measurement employed in the basic method of FIG. 4, or, in variants of the basic method, data indicating the operating mode which can then be verified by applying the inference of operating mode in the basic method.

In one such further embodiment the operating mode is reported from a control unit of the car (it may be assumed that all hybrid vehicles will be equipped with an on-board computer which knows the currently-set operating mode). In another such further embodiment, the vehicle indicates the operating mode indirectly by reporting at least one measurement indicative of vehicle emissions.

Both kinds of reports may be provided. Thus, the vehicle may provide data indicative of emissions from the vehicle and including one or more of:

a thermal measurement of an exhaust part;

a thermal measurement of at least one other part of the vehicle;

a composition measurement of exhaust emissions; and the operating mode in use by the vehicle.

In a preferred embodiment, this data is generated at least partly by a smart exhaust system of the vehicle, described later.

Figure 6:
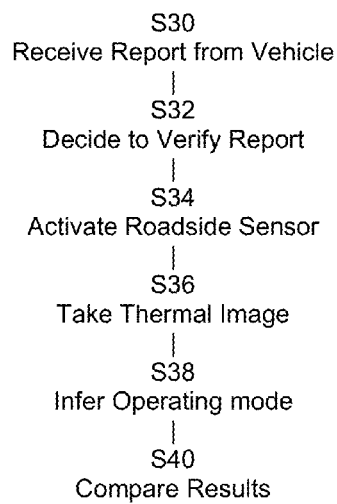
FIG. 6 is a flowchart of process steps in a variant of the method of the present invention.

FIG. 6 outlines this variant of the basic method. Firstly, in a step S30 the central control entity 20 receives a report from the vehicle (for example via a wireless signal transmitted as the vehicle passes a roadside receiver). The central control entity 20 obtains the operating mode according to the vehicle, based on the report. In the case where the report includes the operating mode set by the vehicle on-board computer, the operating mode is simply extracted from the report. In other cases the central control entity 20 will have to infer the operating mode on the basis of other data contained in the report, for example a thermal measurement or chemical measurement relating to the vehicle exhaust. This will be done in a similar manner to that described earlier for a roadside thermal measurement. In either case the report is preferably given a time stamp (from a clock or counter) and a location stamp (from a positioning system such as GPS). It is also preferable for the report from the vehicle to indicate the identity of the vehicle, such as its registration number.

Roadside thermal imaging is still employed, but to reduce the amount of processing, power consumption and communication required, this can now be done on a "sampling" basis as a check of the vehicle operating mode, rather than as the primary determinant of the operating mode. That is, the central control entity 20 may accept the operating mode extracted or determined from the vehicle report most of the time, but in a fixed proportion of cases (such as one in ten), or on a random basis, or if anything about the report looks out of the ordinary (such as a reported operating mode not matching a reported emission reading), the central control entity 20 decides to verify the report in step S32.

Then, in step S34 the central control entity 20 activates the nearest roadside thermal sensor to the vehicle (this may be the next installation along a road being followed by the vehicle). The camera unit 22 of FIG. 3 or 5 (along with the visual camera 28 if present) is then activated so as to capture the thermal image of the vehicle as it passes by (step S36). The same procedure as per the basic method is then followed in order to infer the operating mode on the basis of the thermal data (S38). It is then checked (S40) whether the two results are the same, i.e. whether the operating mode obtained through the vehicle report matches that obtained through the roadside thermal image. As a simple example, an external thermal measurement may indicate that the exhaust system of the vehicle is cool (no warmer than the surroundings). This fact can be used to verify that a zero-emission mode, reported by the vehicle as its current operating mode, is in fact correct. If so, then financial billing can proceed on the basis of the determined operating mode. If not then the vehicle driver/owner may be charged on the basis of the least favorable of the two results, and/or further action may be needed, for example to contact the vehicle owner to advise a check of the vehicle on-board computer or smart exhaust system.

The "smart exhaust system" mentioned above will now be described in more detail. This involves installing within the exhaust system, emission analyzers/sensors or spectral signature sensors. These sensors can be interrogated by roadside equipment sited near the visual/infrared cameras to collect the necessary information to determine the charge and the evidence needed to verify any charging event. Such roadside equipment is preferably located some distance in advance of the cameras, relative to the direction of travel of vehicles on a road. This allows time to collect information from the vehicle, and if deemed necessary (see FIG. 6) to activate the roadside cameras.

It is possible through legislation that all new exhaust systems or new cars would have such an interrogatable exhaust system. Alternatively, it would be possible to incentivize drivers to fit such systems (or buy a suitably-equipped new car) by for example, reducing any emission charge applicable. In this solution it is possible to log the history and track the exhaust emissions. To avoid vehicles failing to send a reading (and thus evade payment), a vehicle which is photographed and does not respond to interrogation could be charged at the highest rate.

Another use of the smart exhaust system would be to aid automated vehicle fault diagnostics and detection to inform the driver/car owner when the emission levels are abnormal and advise/mandate remedial action. Such a multi-functional feature of a new generation of cars would be attractive and help towards managing transport pollution in cities, thus making possible a "pay as you emit" scheme rather than just a "pay as you drive" scheme. In some cities, it may be preferred to implement a combination of pay as you drive and pay as you emit schemes, thus meeting both the objectives of managing congestion and managing pollution.

To summarize, the invention proposes a method of detecting the operating mode of a hybrid vehicle using roadside cameras, the method including the analysis of thermal images of parts of the vehicle and/or exhaust fumes, in combination with associated images of the number plates obtained using visual camera(s) operating in synchronism with a thermal camera and used for vehicle make/model inference and driver identification, the inferred make of the car being used for aforementioned analysis of thermal images.

Any kind of hybrid vehicle offering alternative drive modes including a reduced-emission mode or zero-emission mode can be handled by the scheme provided by embodiments of the present invention. Thus, the present invention is applicable to various types of hybrid vehicle, such as vehicles based on storing chemical energy other than combustible fuel (e.g. fuel cells) or mechanical energy (e.g. flywheels). Dual-fuel vehicles (such as petrol and hydrogen) are counted as hybrids for present purposes. Non-hybrid vehicles are also handled, being treated as having only a single operating mode.

If preferred however, different toll gates could be provided for different types of vehicle, such as conventional ICE-only vehicles, zero-emission vehicles and hybrids, allowing each type to be processed differently.

Various modifications are possible within the scope of the present invention.

In the above embodiments, OCR of a visual image of a number plate (number plate) is performed at the central control unit 20 in order to find out the identity of the vehicle. As one variation, however, it would be possible for the camera unit 22 to perform OCR upon the raw image of the number plate, and supply the OCR-d registration number to the central control unit 20.

In any case, detection of the number plate and of ownership of the vehicle is not essential; it may be sufficient to identify the make/model of car by other means such as shape recognition based on an overall visual image of the vehicle, and to obtain payment of the emission charge by cash or instant debit at a tool booth, near-field payment terminal or the like.

Reference has been made above to a central control unit 20. It should be understood, however, that this term does not necessarily require a single entity but may be distributed, for example in the form of a computer network. As one example, a first computer may be responsible for identifying vehicles and networked to other computers for identifying the available operating modes, determining the operating mode actually in use, setting charges, and so forth.

INDUSTRIAL APPLICABILITY

Embodiments of the present invention make possible a system external to hybrid vehicles which monitors their operating modes and as such enables efficient policing of low-emission zones in future Smart Cities by detecting a widely varying collection of modes. Additionally, by coupling the operations of thermal and visual cameras, unnecessary processing is avoided by allowing precise location of the exhaust with respect to the number plates/ground to be inferred, thereby enabling analysis of the thermal image using fewer samples.

Although a few embodiments have been shown and described, it would be appreciated by those skilled in the art that changes may be made in these embodiments without departing from the principles and spirit of the invention, the scope of which is defined in the claims and their equivalents.

What is claimed is:

1. A method of managing vehicle emissions, comprising:
   receiving at least one measurement relating to a vehicle, including a thermal measurement indicative of emissions from the vehicle;
   detecting an identity of the vehicle and from the identity, determining one or more operating modes available to the vehicle, each operating mode being defined by a specific combination of power or fuel sources;
   inferring, from the thermal measurement, an operating mode in use by the vehicle; and
   calculating an emission charge for the vehicle, based on the operating mode.

2. The method according to claim 1 further comprising providing at least one visual imaging device for use in detecting the identity of the vehicle.

3. The method according to claim 2 wherein the visual imaging device captures an image of a number plate of the vehicle.

4. The method according to claim 1 further comprising providing at least one thermal imaging device for detecting a thermal image of one or more portions of the vehicle indicative of the operating mode, the thermal image being used to derive said thermal measurement.

5. The method according to claim 1 wherein a thermal imaging device detects a thermal image of the vehicle emissions.

6. The method according to claim 1 further comprising the vehicle providing data indicative of emissions from the vehicle and including one or more of:
   a thermal measurement of an exhaust part;
   a thermal measurement of at least one other part of the vehicle;
   a chemical measurement of exhaust emissions; and
   the operating mode in use by the vehicle.

7. The method according to claim 6 further comprising applying a time stamp and location stamp to the data provided from the vehicle.

8. The method according to claim 6 wherein the receiving comprises receiving a thermal measurement taken outside the vehicle and the method further comprising selectively verifying the data provided from the vehicle with the result of inferring based on the thermal measurement taken outside the vehicle.

9. The method according to claim 6, wherein an exhaust system of the vehicle includes at least one sensor providing said data.

10. The method according to claim 1 wherein the at least one measurement further includes a measurement indicative of volume and/or composition of the vehicle emissions.

11. The method according to claim 10 in combination, wherein the measurement indicative of volume and/or composition of the vehicle emissions is provided by analyzing a thermal image of the vehicle emissions.

12. A computer arranged to provide a central entity for pollution control of vehicles, and programmed to:
   receive at least one measurement relating to a vehicle, including a thermal measurement indicative of emissions from the vehicle;
   detect an identity of the vehicle and from the identity, determining one or more operating modes available to the vehicle, each operating mode being defined by a specific combination of power or fuel sources;
   infer, from the thermal measurement, an operating mode in use by the vehicle; and
   calculate an emission charge for the vehicle, based on the operating mode.

13. A pollution management system, comprising:
   a central control unit;
   at least one camera coupled to the central control unit, for taking at least one visual image of a vehicle;
   at least one thermal detector for making a thermal measurement indicative of emissions from the vehicle; and
   at least one database accessible to the central control unit for providing information on vehicle types and operating modes; wherein
   the central control unit is arranged to receive the thermal measurement from the thermal detector; detect an identity of the vehicle using the visual image from the camera and from the detected identity, determine one or more operating modes available to the vehicle; infer, from the thermal measurement, an operating mode in use by the vehicle, based on the operating mode inferred; and calculate an emission charge for the vehicle, based on the operating mode.

* * * * *